United States Patent [19]

Frankel et al.

[11] 4,303,414
[45] Dec. 1, 1981

[54] AZIDO ADDITIVES FOR LIQUID HYDROCARBON MOTOR FUELS

[75] Inventors: Milton B. Frankel, Tarzana; Joseph E. Flanagan, Woodland Hills, both of Calif.

[73] Assignee: Rockwell International Corporation, El Segundo, Calif.

[21] Appl. No.: 216,394

[22] Filed: Dec. 15, 1980

[51] Int. Cl.$^3$ ............................................... C10L 1/22
[52] U.S. Cl. ........................................... 44/63; 44/64
[58] Field of Search ...................................... 44/63, 64

[56] References Cited

U.S. PATENT DOCUMENTS 2,115,275  4/1938  Moran et al. .......................... 44/64
3,520,665  7/1970  McConnell ............................ 44/64

Primary Examiner—Jacqueline V. Howard
Attorney, Agent, or Firm—H. F. Hamann; Harry B. Field

[57] ABSTRACT

This invention relates to liquid hydrocarbon motor fuels improved by the addition of an azido compound. Specifically, the azido compounds of the present invention have the following general formulas $N_3$—$R_2$, $N_3$—$R_2$—$N_3$, $N_3$—$R_3$—O—$R_4$—$N_3$, $N_3$—$R_3$—$CO_2$—$R_4$—$N_3$,

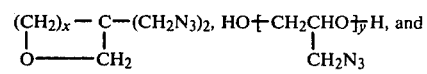
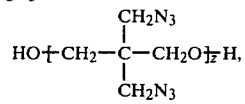

wherein R is an alkyl, alkyl hydroxy, primary alkyl ether, and alkyl ester and mixtures thereof; $R_2$ is an alkyl or alkyl hydroxy, $R_3$ and $R_4$ are the same or different and comprise lower alkyl radicals and mixtures thereof; x is an integer from 1 to 5' y is an integer from 3 to about 20; and z is an integer from 3 to 20.

5 Claims, No Drawings

AZIDO ADDITIVES FOR LIQUID HYDROCARBON MOTOR FUELS

BACKGROUND OF THE INVENTION

1. Field of the Invention

This invention relates to liquid hydrocarbon motor fuel additives and, more specifically, to liquid hydrocarbon motor fuels improved by the addition of a minor proportion of a mono and/or di-azido additive.

2. Description of the Prior Art

Combustion and thermal efficiency of motor fuels have become of primary importance in the automotive industry. Not only is it vital to obtain the optimum amount of energy out of fuels, but it is similarly important to burn these fuels completely without the formation of soot and other pollutants. It has been found that various additives can be introduced into diesel or gasoline fuels to enhance the combustion rate, improve octane ratings for gasoline and cetane ratings for diesel fuel, and in general improve the quality of combustion within an internal or Stirling combustion engine.

Additionally, it has been found that the ignition quality of fuel can be improved by the addition of small amounts of certain adjuvants which act as ignition accelerators. This offers a means for improving the better grades of diesel fuels and of gasolines, and as a result widens the range of available fuel qualities by raising the ignition quality of lower grades of fuels to a point where they can be satisfactorily used.

SUMMARY OF THE INVENTION

In accordance with the present invention, there is provided a family of liquid hydrocarbon motor fuel additives known as azides. Specifically, the azido compounds of the present inventions have the following general formulas $N_3-R_1$, $N_3-R_2-N_3$, $N_3-R_3-O-R_4-N_3$, $N_3-R_3OCO_2-R_4-N_3$,

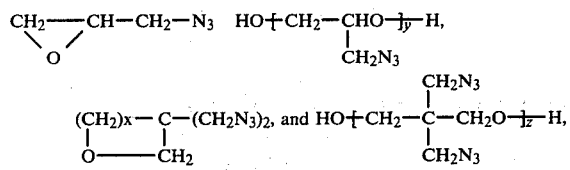

wherein $R_1$ is an alkyl, alkyl hydroxy, primary alkyl ether, alkyl esters, nitro alkyl, nitrato alkyl, and mixtures thereof; $R_2$ is a lower alkyl on mixtures thereof, $R_3$ and $R_4$ are the same or different and comprise lower alkyl radicals and mixtures thereof; x is an integer from 1-5; y is an integer from 3 to about 20 and preferably from 5-10; and z is an integer from 3 to 20 and preferably from 5-10. These adjuvants have been particularly useful in increasing combustions and thermal efficiency and reducing pollutants generated during combustion.

OBJECTS OF THE INVENTION

Therefore, it is an object of the present invention to provide a liquid hydrocarbon motor fuel having fuel having fuel additives capable of increasing combustion efficiency.

Another object of the present invention is to provide a liquid hydrocarbon motor fuel having fuel additives capable of improving thermal efficiency.

Yet another object of the present invention is to provide a liquid hydrocarbon motor fuel having an additive capable of enhancing ignition characteristics.

Still another object of the present invention is to provide a liquid hydrocarbon motor fuel having an additive capable of decreasing pollution by-products generated during combustion.

Another object of the present invention is to provide a liquid hydrocarbon motor fuel having an additive capable of increasing the octane rating of gasoline.

A further object of the present invention is to provide a liquid hydrocarbon motor fuel additive capable of enhancing the cetane rating of diesel fuel.

Other objects, advantages and novel features of the present invention will become apparent from the following detailed description of the invention.

DESCRIPTION OF THE PREFERRED EMBODIMENTS

In accordance with the present invention, there is provided a family of liquid hydrocarbon motor fuel additives known as azides. Specifically, it has been found that the alkyl azides compounds of the general formula $N_3R_1$, the di-azido compounds of the general formula $N_3-R_2-N_3$, the di-azido ethers and esters of the general formula $N_3-R_3-O-R_4-N_3$ and $N_3-R_3-CO_2-R_4-N_3$ respectively, the glycidal azide monomer and its polymer of the general formulas

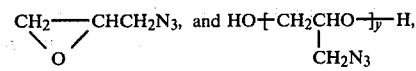

and the substituted cyclic polymethylene of the general formula

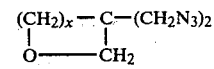

and its polymer

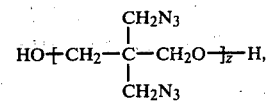

and mixtures thereof have been particularly useful in increasing combustion efficiency and reducing pollutants generated in internal combustion and Stirling-type engines.

It has been found that for the above azides $R_1$ is an alkyl, alkyl hydroxy, primary alkyl ether, alkyl ester, nitro alkyl, nitrato alkyl and mixtures thereof. $R_2$ is a lower alkyl or mixtures of lower alkyls. The preferred lower alkyls are methyl, ethyl, propyl and butyl, while the most preferred are methyl and ethyl. $R_3$ and $R_4$ are the same or different and comprise lower alkyl radicals and mixtures thereof. X is an integer from 1 to 5, y is an integer from about 3 to about 20 and preferably from 5 to 10, and z is an integer from 3 to 20 and preferably from 5 to 10.

The above adjuvants can be added to the petroleum motor fuel in any combination and in quantities ranging from greater than 0.0 to about 1.0 volume percent. The preferred volume percent ranges from about 0.2 to about 0.4.

The following general syntheses are given for the preferred azido species. They are provided solely for illustration purposes and are not meant to serve as limitations on the present invention:

General Synthetic Method for Preparation of Alkyl Azides

By reaction of alkyl halides, sulfonates, and nitrates with sodium azide in dipolar aprotic solvents such as dimethylformamide (DMF) and dimethyl sulfoxide (DMSO):

$A = Cl, Br, CH_3C_6H_4SO_2, DNO_2$.

Alkyl Hydroxy

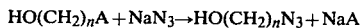

where n is an integer from 1–5.

Alkyl Ethers

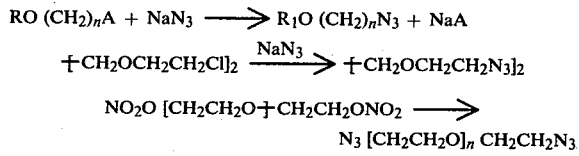

where n is an integer from 1–5.

Alkyl Esters

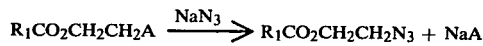

Nitro Alkyl Esters

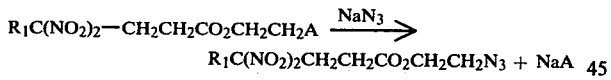

Di-Azido Alkyl

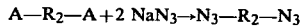

Di-Azido Ether

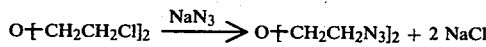

Di-Azido Ester

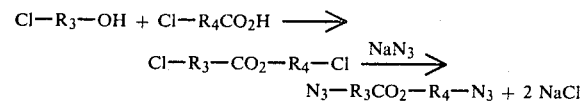

Thus, it is apparent that there is provided by this invention adjuvants for liquid hydrocarbon motor fuels.

Obviously, many modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. A liquid hydrocarbon motor fuel comprising a minor portion of an azido compound of the general $N_3R_1$, wherein $R_1$ represents a radical selected from the group consisting of nitro alkyls, nitrado alkyls, and mixtures thereof.

2. A liquid hydrocarbon motor fuel comprising a minor proportion of glycidyl azide of the formula

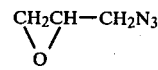

or its polymer of the general formula

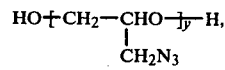

wherein y is an integer between about 3 and about 20.

3. The liquid hydrocarbon motor fuel of claim 2 wherein y is an integer from about 5 to about 10.

4. A liquid hydrocarbon motor fuel comprising a minor proportion of an azido substituted cyclic polymethylene oxide of the general formula

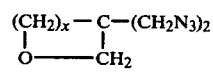

or its polymer of the general formula

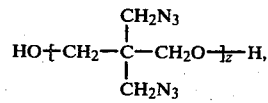

wherein x is an integer from 1 to 5 and wherein z is an integer from 3 to 20.

5. The liquid hydrocarbon motor fuel of claim 4 wherein z is an integer from about 5 to about 10.

* * * * *